(12) United States Patent
Huang et al.

(10) Patent No.: US 12,372,452 B1
(45) Date of Patent: Jul. 29, 2025

(54) METHOD AND DEVICE FOR DETERMINING CONCENTRATION OF SURFACTANT SOLUTION FOR OIL DISPLACEMENT BY IMBIBITION

(71) Applicant: YAN' AN UNIVERSITY, Shaanxi (CN)

(72) Inventors: Feifei Huang, Shaanxi (CN); Yandong Yang, Shaanxi (CN); Shaofei Kang, Shaanxi (CN); Chunsheng Pu, Shaanxi (CN); Hengli Wang, Shaanxi (CN)

(73) Assignee: YAN'AN UNIVERSITY, Yan'an (CN)

( * ) Notice: Subject to any disclaimer, the term of this patent is extended or adjusted under 35 U.S.C. 154(b) by 0 days.

(21) Appl. No.: 19/095,881

(22) Filed: Mar. 31, 2025

(30) Foreign Application Priority Data

Sep. 24, 2024 (CN) .......................... 202411330025.8

(51) Int. Cl.
  *G01N 13/04* (2006.01)
  *G01N 33/26* (2006.01)
  (Continued)

(52) U.S. Cl.
  CPC ............. *G01N 13/04* (2013.01); *G01N 33/26* (2013.01); *C09K 8/584* (2013.01); *E21B 43/16* (2013.01); *G01N 33/2823* (2013.01)

(58) Field of Classification Search
  CPC .... G01N 13/04; G01N 33/26; G01N 33/2823; E21B 43/16; C09K 8/584
  See application file for complete search history.

(56) References Cited

U.S. PATENT DOCUMENTS 10,023,787 B2* 7/2018 Benoit .................. C09K 8/584
2017/0322132 A1* 11/2017 Potty ..................... G01N 11/08
(Continued)

FOREIGN PATENT DOCUMENTS

CN 102393444 A 3/2012
CN 104749071 A 7/2015
(Continued)

OTHER PUBLICATIONS

Notification to Grant Patent Right for Invention, Chinese Application No. 202411330025.8, mailed Nov. 29, 2024 (3 pages).
(Continued)

*Primary Examiner* — Nathaniel J Kolb
(74) *Attorney, Agent, or Firm* — HOWARD M COHN and Associates, LLC

(57) ABSTRACT

Disclosed is a method and device for determining the surfactant concentration for oil displacement by imbibition. The method includes the following steps: providing a tank for holding the surfactant solution and a capillary tube; adding the surfactant solution with a first preset concentration into the tank; injecting crude oil into the capillary tube, a liquid level difference ΔH is generated between a liquid level of the capillary tube and the liquid level of the tank; recording data of the ΔH varying over time, and calculating an imbibition dynamic and resistance ratio of the surfactant solution with the first preset concentration based on the data; repeating the steps for each surfactant solution with different concentration; and determining the optimal concentration under the best oil displacement effect of the surfactant solution based on the imbibition dynamic and resistance ratios of the surfactant solutions with different concentration.

3 Claims, 12 Drawing Sheets

(51) Int. Cl.
  *C09K 8/584* (2006.01)
  *E21B 43/16* (2006.01)
  *G01N 33/28* (2006.01)

(56) References Cited

U.S. PATENT DOCUMENTS

2018/0327651 A1 11/2018 Piri et al.
2022/0049152 A1* 2/2022 Ayirala .................. E21B 43/16

FOREIGN PATENT DOCUMENTS

| | | |
|---|---|---|
| CN | 105938084 A | 9/2016 |
| CN | 107037161 A | 8/2017 |
| CN | 107511189 A | 12/2017 |
| CN | 113533033 A | 10/2021 |
| CN | 114577676 A | 6/2022 |
| DE | 3516406 A1 | 11/1986 |
| KR | 20210118265 A | 9/2021 |

OTHER PUBLICATIONS

CNIPA, Office Action issued for Chinese Application No. 202411330025.8, mailed Nov. 8, 2024 (14 pages).

* cited by examiner

METHOD AND DEVICE FOR DETERMINING CONCENTRATION OF SURFACTANT SOLUTION FOR OIL DISPLACEMENT BY IMBIBITION

FIELD

The disclosure relates to the technical field of oil and gas field, in particular to a method and device for determining concentration of a surfactant solution for oil displacement by imbibition.

BACKGROUND OF THE INVENTION

With the decreasing resources of conventional oil reservoirs, tight oil reservoirs have gradually become an important alternative for oil and gas exploration and development. In China, most tight oil reservoirs are of continental sedimentation, generally exhibiting low reservoir energy. After large-scale hydraulic fracturing, the initial production capacity is relatively high. However, as the reservoir energy decreases, production drops sharply, necessitating water injection to replenish reservoir energy. Due to the dense matrix and the natural abundant microcracks, along with the complexity of the artificial fracture network after fracturing, injected water tends to channel along the fracture system, making it difficult to displace the residual oil directly by displacement. Meanwhile, due to the small pore throats, capillary forces are significant, resulting in injected water spontaneously imbibing into tiny pores under capillary action to displace the residual oil. To enhance this imbibition effect, anionic or nonionic surfactants are commonly added to the injected water, which is a process known as oil displacement by imbibition of surfactant solution.

The addition of surfactants can reduce the wetting angle of the water phase (enhancing reservoir hydrophilicity) while lowering interfacial tension. Within an appropriate concentration range, the reduction in both parameters is positively correlated with surfactant concentration. The formula for calculating capillary force is:

$$p_c = \frac{2\sigma\cos\theta}{r},$$

where $P_c$ is the capillary force; $\sigma$ is the oil-water interfacial tension; $\theta$ is the wetting angle; and r is the capillary radius. Although a larger capillary force is needed to enhance imbibition, it can also significantly increase resistance during the oil displacement phase due to the Jamin's effect. Thus, the concentration of surfactants has a significant impact on the effectiveness of imbibition and displacement. In practice, it is often necessary to obtain the optimal surfactant concentration for oil displacement by imbibition through indoor core displacement experiments.

However, due to the low permeability of tight reservoir cores, the pressure required for displacement experiments is typically above 15 MPa, and the process takes a long time, often exceeding three days per experiment. Consequently, these experiments are generally entrusted to specialized laboratories, resulting in high costs and long cycles, and making it difficult to provide timely guidance for field applications. In summary, the existing methods for determining surfactant concentrations and their effects on displacement are costly and time-consuming.

BRIEF DESCRIPTION OF DRAWINGS

To describe technical solutions in embodiments of the disclosure more clearly, accompanying drawings required in description of the embodiments will be briefly introduced below. Apparently, the accompanying drawings in the following description merely show some embodiments of the disclosure, and a person of ordinary skill in the art can still derive other accompanying drawings from structures shown in these accompanying drawings without creative efforts.

DETAILED DESCRIPTION OF THE INVENTION

The following will provide a further explanation of the present disclosure in conjunction with the accompanying drawings.

First Embodiment

Figure 1:
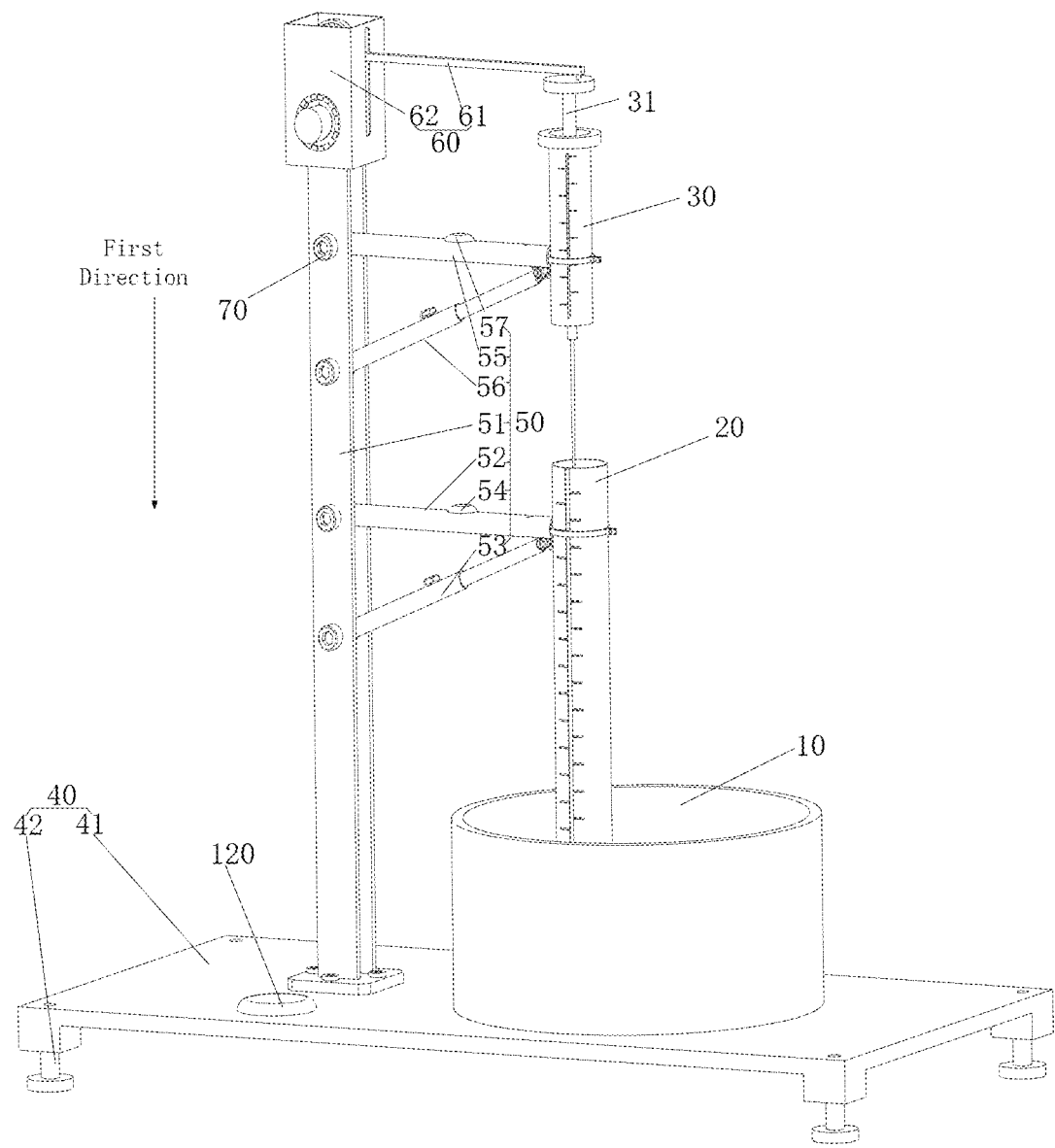
FIG. 1 is a schematic structural diagram of a device for determining concentration of a surfactant solution for oil displacement by imbibition according to the first embodiment.
Figure 2:
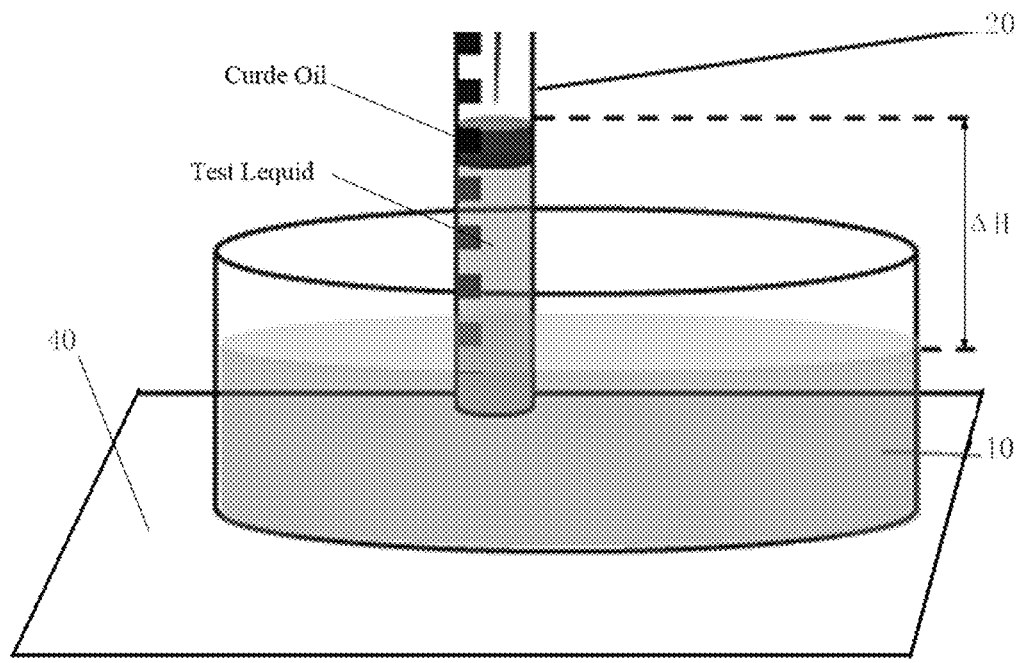
FIG. 2 is a diagram showing a liquid level difference ΔH between crude oil level and the surfactant solution level in FIG. 1.

As shown in FIGS. 1 and 2, a device for determining concentration of a surfactant solution for oil displacement by imbibition is provided, which includes a water tank 10, a capillary tube 20, and a syringe 30. The water tank 10 is configured to hold the tested liquid, such as surfactant solutions or water. The capillary tube 20 is arranged with one end located inside the water tank 10. A scale is set on the capillary tube 20. The syringe 30 includes an injection end. The injection end extends into the capillary tube 20 from the other end of the capillary tube 20. The syringe 30 is configured to inject a certain amount of crude oil into the capillary tube 20. The liquid level of the tested liquid in the water tank 10 is higher than the minimum scale of the capillary tube 20 to facilitate the reading of the level difference ΔH between the liquid levels inside and outside the capillary tube 20. After the certain amount of crude oil is injected into the capillary tube 20, there is a liquid level difference ΔH between the liquid level of the capillary tube 20 and that of the water tank 10. The liquid level difference ΔH is a dynamic value that varies over time. An imbibition dynamic and resistance ratio of the tested liquid can be calculated based on ΔH, and the imbibition dynamic and resistance ratio can be used to determine the oil displacement effectiveness of the tested liquid. By comparing the imbibition dynamic and resistance ratios of different concentrations and/or types of the tested liquids, the oil displacement effectiveness can be evaluated.

In the above arrangement, the imbibition dynamic and resistance ratio corresponding to the tested liquid is calculated through the liquid level difference ΔH, and the oil displacement effectiveness is determined by comparing the imbibition dynamic and resistance ratios. The larger the imbibition dynamic and resistance ratio, the better the corresponding oil displacement effectiveness of the tested liquid. This configuration enables the rapid determination of the impact of surfactant concentrations on oil displacement effectiveness, thereby shortening the time required to identify the optimal concentration of the surfactant solution and improving the efficiency of surfactant screening while also reducing costs.

It should be noted that by comparing the imbibition dynamic and resistance ratios of different types of tested liquids, the best tested liquid can be selected. By comparing the imbibition dynamic and resistance ratios of different concentration solutions, the optimal surfactant concentration can be identified.

Specifically, as shown in FIG. 1, in one embodiment, the device for determining the concentration of surfactant solution for oil displacement by imbibition further includes a supporting and leveling mechanism 40. The water tank 10 is placed on the supporting and leveling mechanism 40, which is configured to support the water tank 10 and adjust the level of the water tank 10.

In the above arrangement, the supporting and leveling mechanism 40 allows the water tank 10 to be leveled, ensuring that the liquid inside the water tank 10 remains horizontal. This ensures the accuracy of readings on the scale of the capillary tube 20, which in turn ensures the precision of calculating the imbibition dynamic and resistance ratio of the tested liquid.

It should be noted that if the water tank 10 is not leveled, the liquid inside will tilt, affecting the accuracy of the readings on the scale of the capillary tube 20, which will subsequently affect the accuracy of the liquid level difference ΔH reading and the calculation precision of the imbibition dynamic and resistance ratio of the tested liquid, thereby impacting the screening results.

Specifically, as shown in FIG. 1, in one embodiment, the supporting and leveling mechanism 40 includes a base 41 and a plurality of anchor bolts 42. The base 41 is configured to support the water tank 10. The plurality of anchor bolts 42 are arranged at the bottom of the base 41 and are threadedly connected to the base 41. Adjusting the anchor bolts 42 allows for leveling the base 41.

Specifically, as shown in FIG. 1, a third spirit level 120 is arranged on the base 41 to assist in leveling the water tank 10 in conjunction with the anchor bolts 42.

In the above arrangement, the adjustment of one or several anchor bolts 42 can ensure that the base 41 is in a horizontal position, thus ensuring that the water tank 10 placed on the base 41 is leveled. This ensures the accuracy of calculating the imbibition dynamic and resistance ratio of the tested liquid, leading to accurate identification of the optimal concentration of surfactant solution.

Specifically, as shown in FIG. 1, in one embodiment, the base 41 is a rectangular plate, the number of the anchor bolts 42 is four, and the four anchor bolts 42 are respectively disposed at four corner positions of the rectangular plate.

Of course, the base 41 may be provided with other shapes according to actual conditions, such as a circular plate. The number of the anchor bolts 42 may be set to three or five or more, and the plurality of anchor bolts 42 may be evenly spaced at the bottom of the circular plate.

Specifically, as shown in FIG. 1, in one embodiment, the device further includes a suspension leveling mechanism 50, which is disposed on the base 41. The suspension leveling mechanism 50 includes a metal bracket 51, a capillary tube holder 52, a first telescopic rod 53, and a first spirit level 54. The metal bracket 51 is arranged on the base 41, and one end of the capillary tube holder 52 is rotatably connected to the metal bracket 51, while the other end of the capillary tube holder 52 is configured to hold the capillary tube 20. One end of the first telescopic rod 53 is rotatably connected to the capillary tube holder 52, and the other end of the first telescopic rod 53 is rotatably connected to the metal bracket 51. The first spirit level 54 is disposed on the capillary tube holder 52.

In the above arrangement, the telescopic function of the first telescopic rod 53 allows for the adjustment of the rotation angle of the capillary tube holder 52. By observing the first spirit level 54, the capillary tube holder 52 can be leveled, ensuring that the capillary tube 20 hangs vertically inside the water tank 10. This ensures the accuracy of readings on the scale of the syringe 30, which in turn ensures the precision of calculating the imbibition dynamic and resistance ratio of the tested liquid.

Figure 3:
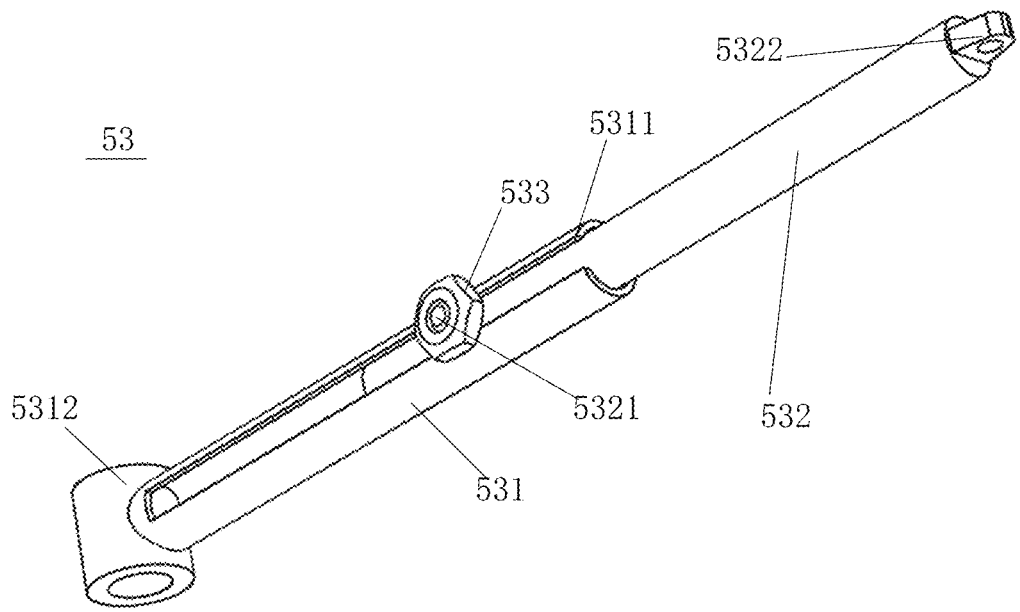
FIG. 3 is a schematic structural diagram of a first telescopic rod in FIG. 1.
Figure 4:
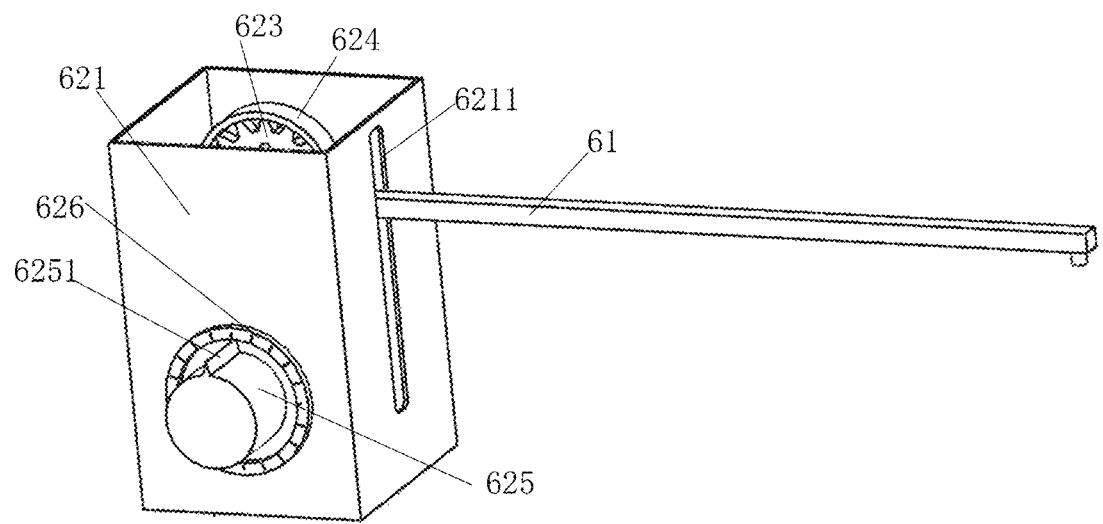
FIG. 4 is a schematic structural diagram of an injection volume control mechanism in FIG. 1.
Figure 5:
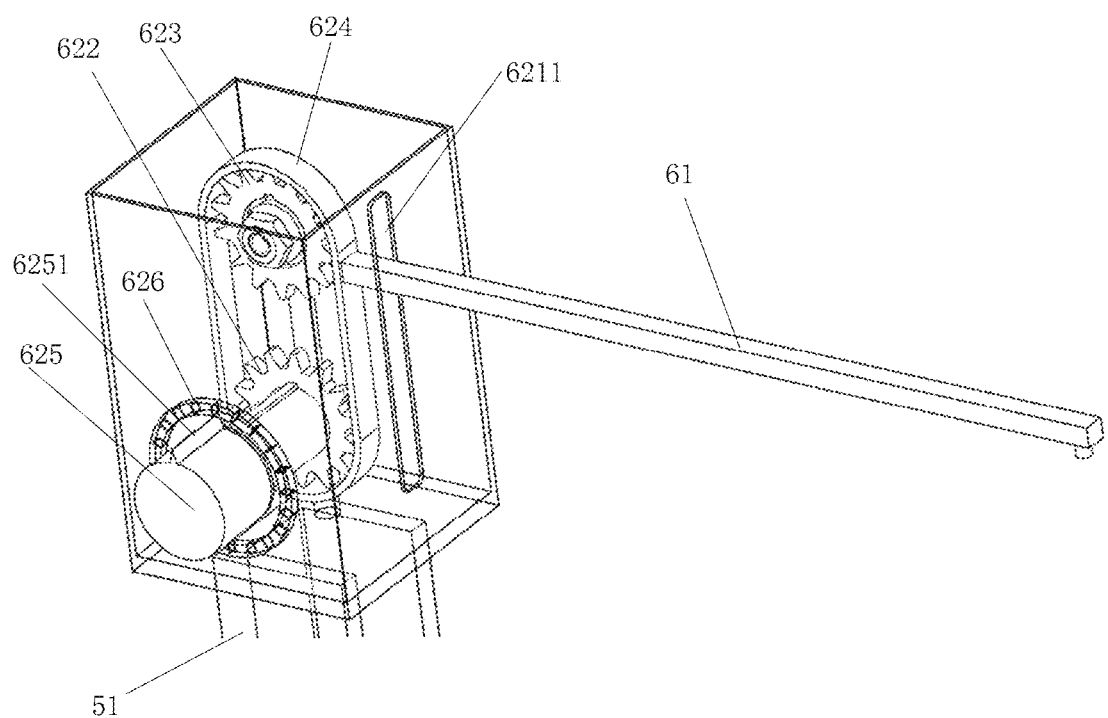
FIG. 5 is a perspective view of the injection volume control mechanism in FIG. 1.
Figure 6:
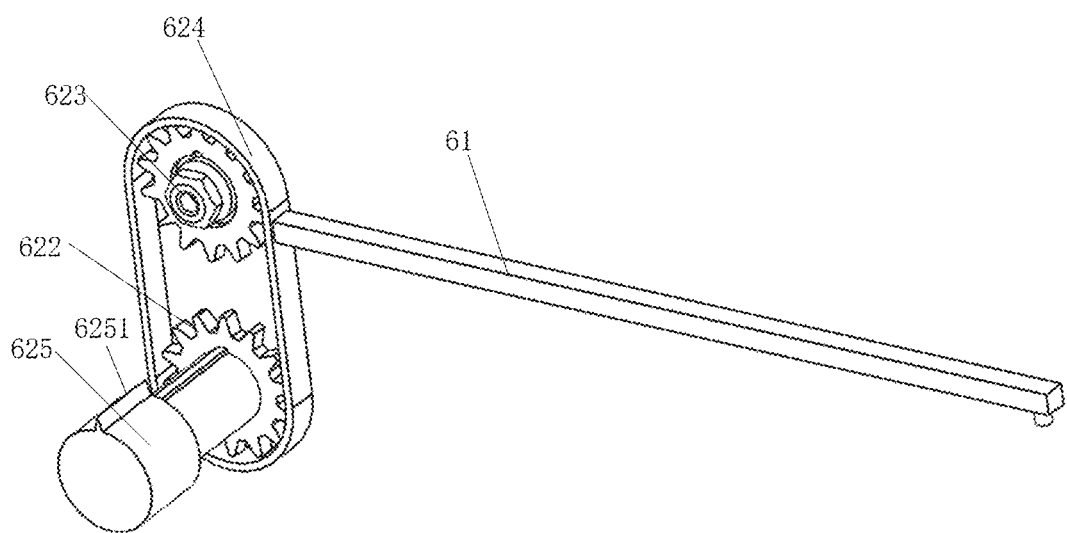
FIG. 6 is a schematic diagram of connection relationship among a first drive wheel assembly, a second drive wheel assembly, a transmission chain, a knob, and a piston linkage rod in FIG. 4.

Specifically, as shown in FIG. 3, in one embodiment, the first telescopic rod 53 includes a first outer cylinder 531 and a first inner cylinder 532 that is telescopically arranged within the first outer cylinder 531. The first outer cylinder 531 is connected to the metal bracket 51, while the first inner cylinder 532 is connected to the capillary tube holder 52. A first stud 5321 is arranged on the outer periphery of the first inner cylinder 532, and a first opening sliding groove 5311 is arranged on the outer periphery of the first outer cylinder 531 along the axial direction. The first stud 5321 is slidably engaged with the first opening sliding groove 5311, allowing the first outer cylinder 531 is telescopically engaged with the first inner cylinder 532. One end of the first stud 5321 extends out of the first opening sliding groove 5311. The first telescopic rod 53 further includes a first nut 533. The first nut 533 is threadedly engaged with one end of the first stud 5321 extending out of the first opening sliding groove 5311. When the first inner cylinder 532 is moved to the position where the capillary holder 52 is leveled, the first nut 533 is tightened to fix the relative position between the first inner cylinder 532 and the first outer cylinder 531.

Specifically, as shown in FIG. 3, in one embodiment, one end of the first outer cylinder 531 is provided with a first connecting sleeve 5312, and the first connecting sleeve 5312 is configured for rotatably connecting with the metal bracket 51. A connecting ear plate 5322 is disposed at one end of the first inner cylinder 532 for rotatably connecting with the capillary tube holder 52.

Specifically, as shown in FIG. 1, in one embodiment, the suspension leveling mechanism 50 further includes a syringe holder 55, a second telescopic rod 56, and a second spirit level 57. One end of the syringe holder 55 is rotatably disposed on the metal bracket 51, and the other end of the syringe holder 55 is configured to holder the syringe 30. One end of the second telescopic rod 56 is rotatably connected to the syringe holder 55, the other end of the second telescopic rod 56 is rotatably connected to the metal bracket 51, and the second spirit level 57 is disposed on the syringe holder 55.

In the above arrangement, the syringe holder 55 can be levelled using the telescopic function of the second telescopic rod 56, which ensures that the syringe holder 55 can suspend the syringe 30 vertically, and the syringe 30 can be adjusted to the proper injection position, thereby preventing the syringe 30 from injecting crude oil out of the capillary tube 20.

Specifically, as shown in FIG. 1, in one embodiment, the structure of the second telescopic rod 56 is the same as that of the first telescopic rod 53.

Further, referring to FIG. 3, the second telescopic rod includes a second outer cylinder and a second inner cylinder that is telescopically arranged within the second outer cylinder. The second outer cylinder is rotatably connected with the metal bracket, and the second inner cylinder is rotatably connected with the syringe. A second stud is arranged on the outer periphery of the second inner cylinder, and a second opening sliding groove is arranged on the outer periphery of the second outer cylinder along the axial direction. The second stud is slidably engaged with the second opening sliding groove, allowing the second outer cylinder is telescopically engaged with the second inner cylinder. One end of the second stud extends out of the second opening sliding groove, and the second telescopic rod further includes a second nut. The second nut is threadedly engaged with one end of the second stud extending out of the second opening sliding groove. When the second inner cylinder is moved to the position where the capillary holder is leveled, the second nut is tightened to fix the relative position between the second inner cylinder and the second outer cylinder. One end of the second outer cylinder is provided with a second connecting sleeve, and the second connecting sleeve is configured for rotatably connecting with the metal bracket. A connecting ear plate is disposed at one end of the second inner cylinder for rotatably connecting with the capillary holder 52.

Figure 8:
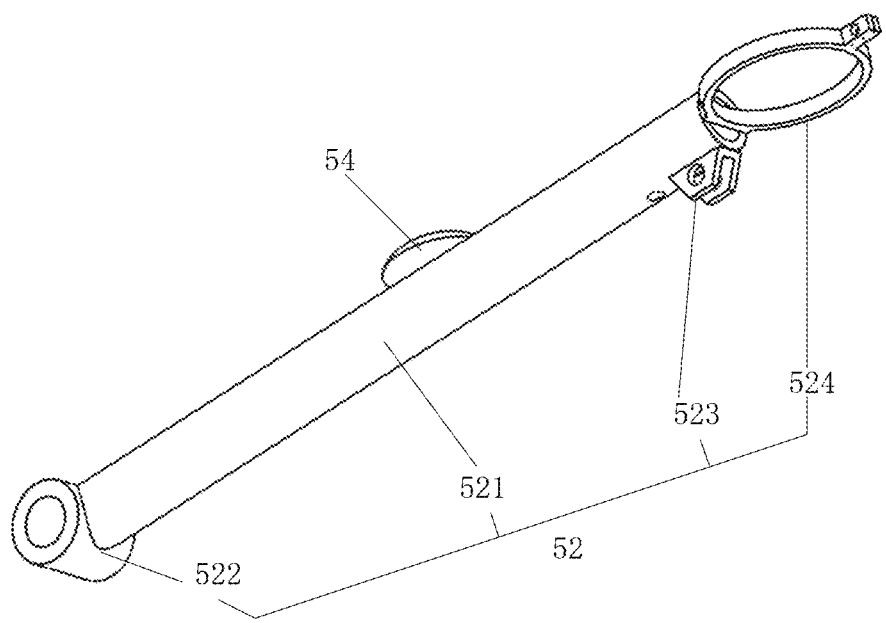
FIG. 8 is a schematic structural diagram of a capillary tube holder in FIG. 1.

Specifically, as shown in FIG. 8, in one embodiment, the capillary tube holder 52 includes a connecting cylinder 521, a rotating cylinder 522, a connecting seat 523, and a clamp 524. The rotating cylinder 522 and the clamp 524 are respectively arranged at both ends of the connecting cylinder 521. The rotating cylinder 522 is configured for rotatably connecting to the metal bracket 51, and the clamp 524 is configured clamping the capillary tube 20 tightly. The connecting seat 523 is arranged at the bottom of the connecting cylinder 521 for rotatably connecting to the first telescopic rod 53.

It should be noted that the other end of the capillary tube holder 52 uses the clamp 524 to tightly hold the outer peripheral wall of the capillary tube 20. In this disclosure, the syringe 30 is located directly above the capillary tube 20, and the structure of the syringe holder 55 is the same as that of the capillary tube holder 52. The other end of the syringe holder 55 also uses a clamp to tightly hold the outer peripheral wall of the syringe 30. The structure of the clamp is of existing technology and will not be elaborated here.

It should be noted that the metal bracket 51 is provided with four threaded holes, and four first connecting bolts 70 are correspondingly passed through the four threaded holes. From bottom to top, the four first connecting bolts 70 are respectively rotatably connected to the first telescopic rod 53, the capillary tube holder 52, the second telescopic rod 56, and the syringe holder 55.

Figure 9:
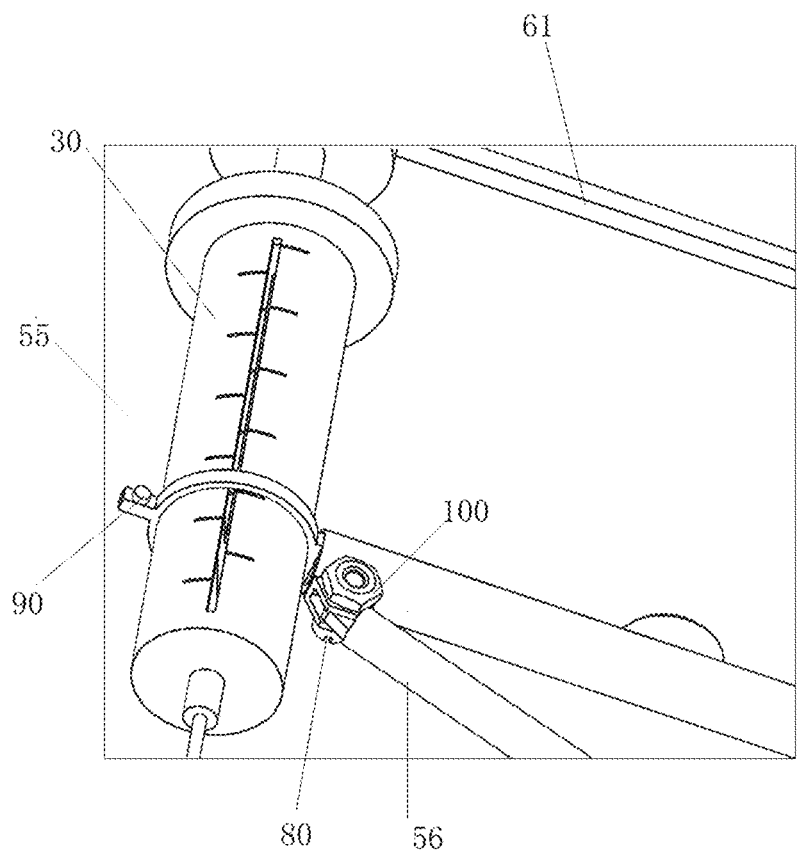
FIG. 9 is a partial schematic diagram of connection relationship between a syringe holder and a syringe in FIG. 1.
Figure 10:
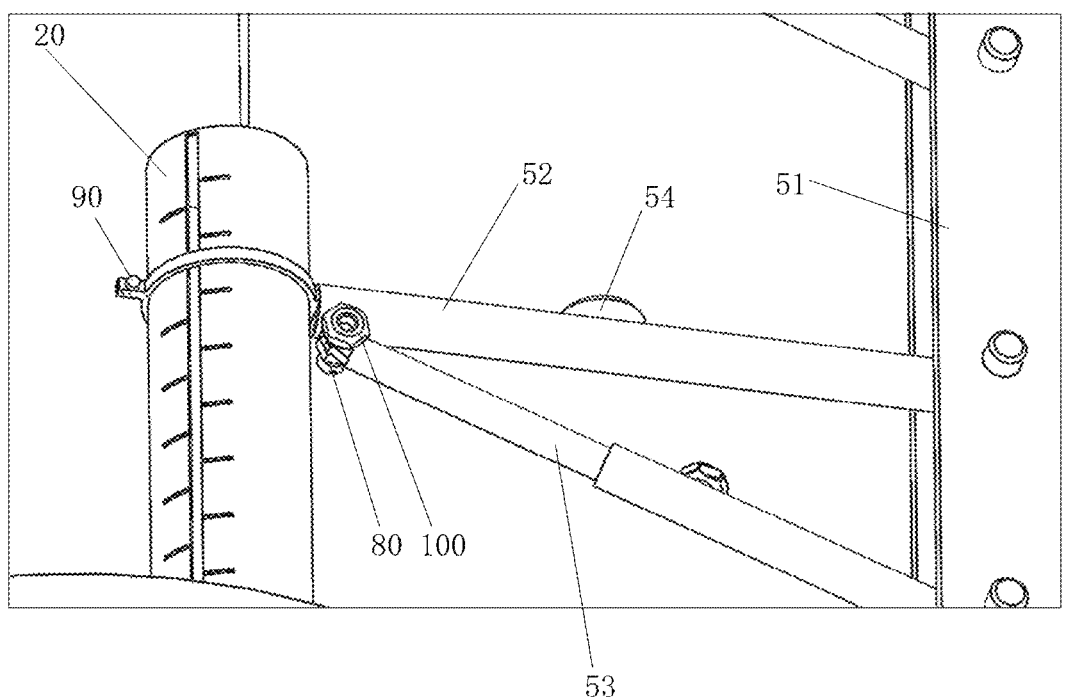
FIG. 10 is a partial schematic diagram of connection relationship between the capillary tube holder and a capillary tube in FIG. 1.

It should be noted that, as shown in FIGS. 9 and 10, in one embodiment, a second connecting bolt 80 is passed through the connection between the second telescopic rod 56 and the syringe holder 55, and one end of the second connecting bolt 80 is provided with a connecting nut 100. The second connecting bolt 80 is passed through the connection between the first telescopic rod 53 and the capillary tube holder 52, and one end of the second connecting bolt 80 is also provided with the connecting nut 100. The clamp 524 is locked by a third connecting bolt 90.

Specifically, as shown in Figures. 4 to 7, in one embodiment, the device further includes an injection volume control mechanism 60 connected to the piston 31 of the syringe 30 for controlling the moving distance of the piston 31, thereby accurately controlling the injection amount per injection. This replaces manual direct operation of the syringe 30 for oil injection, thereby improving the accuracy of oil injection.

Specifically, as shown in FIGS. 4 to 7, in one embodiment, the injection volume control mechanism 60 includes a piston linkage rod 61 and a knob mechanism 62. The piston linkage rod 61 is connected to the piston 31 of the syringe 30, and the piston 31 is capable of moving synchronously with the piston linkage rod 61. The knob mechanism 62 is arranged at the top of the metal bracket 51. The knob mechanism 62 includes a knob 625, which can drive the piston linkage rod 61 to move a preset distance when the knob 625 is rotated to a preset angle, thus injecting a preset amount of crude oil into the capillary tube 20.

In the above arrangement, the moving distance of the piston linkage rod 61 and the piston 31 can be accurately controlled by rotating the knob 625, so that the injection amount of the syringe 30 can be accurately controlled by rotating the knob 625. In this way, field personnel do not need to directly operate the piston 31 to inject crude oil, thereby improving the convenience of use of the device and improving the accuracy of the oil injection amount of the device.

Specifically, as shown in FIGS. 4 to 7, in one embodiment, the knob mechanism 62 further includes a housing 621, a first drive wheel assembly 622, a second drive wheel assembly 623, and a transmission member 624. The housing 621 is arranged at the top of the metal bracket 51, and a limiting sliding groove 6211 is provided on the side of the housing 621 close to the syringe 30. The piston linkage rod 61 is capable of sliding back and forth in the limiting sliding groove 6211 along the first direction. The limiting sliding groove 6211 can restrict the sliding position of the piston linkage rod 61 within its limits. The first drive wheel assembly 622 is rotatably arranged inside the housing 621, and the second drive wheel assembly 623 is also rotatably arranged inside the housing 621. The second drive wheel assembly 623 is positioned directly above the first drive wheel assembly 622. The transmission member 624 is sleeved on the first drive wheel assembly 622 at one end and meshes with it, while the other end of the transmission member 624 is sleeved on the second drive wheel assembly 623 and meshes with it. One end of the piston linkage rod 61 is connected to the transmission member 624. The knob 625 partially extends into the housing 621 and is connected to the first drive wheel assembly 622. The rotation of the knob 625 is capable of driving the first drive wheel assembly 622 to rotate, causing the transmission member 624 to transmit between the first drive wheel assembly 622 and the second drive wheel assembly 623, thereby driving the piston linkage rod 61 to slide along the first direction within the limiting sliding groove.

In the above arrangement, the reciprocally movement distance of the piston linkage rod 61 in the vertical direction (the first direction) is controlled by reciprocally movement of the transmission member 624 between the second drive wheel assembly 623 and the first drive wheel assembly 622.

Specifically, the distance traveled by the transmission member 624 is controlled by controlling the angular displacement of the first drive wheel assembly 622, thereby controlling the moving distance of piston linkage rod 61 and piston 31. Thus, the oil injection amount of the syringe 30 is controlled to meet the preset oil injection amount requirement.

In addition, the limiting sliding groove 6211 is a strip-shaped groove. One end of the limiting sliding groove 6211 is close to the first driving wheel assembly 622, and the other end of the limiting sliding groove 6211 is close to the second driving wheel assembly 623. The two ends of the limiting sliding groove 6211 contact with the piston linkage rod 61 to limit the piston linkage rod 61.

It should be noted that the syringe 30 is marked with scale lines for the injection volume, and a pointer 6251 is disposed on the periphery of the knob 625. A scale plate 626 with volume scale lines is provided on the housing 621, which consistent with the scale lines on the syringe 30. The knob 625 is rotatably passed through the scale plate 626 and is concentric with it. When the pointer 6251 rotates to the volume scale line corresponding to the preset injection volume on the scale plate 626, the knob mechanism 62 drives the piston linkage rod 61 to move the preset distance, allowing the syringe 30 to inject the preset amount of crude oil.

Specifically, as shown in FIGS. 4 to 7, in one embodiment, the housing 621 includes an outer shell 6212 and a support frame 6213. The support frame 6213 is disposed inside the outer shell 6212. The support frame 6213 is provided with a first rotating stud and a second rotating stud. The first drive wheel assembly 622 includes a first drive wheel 6221 and a first limit nut 6222. The first drive wheel 6221 is rotatably sleeved on the first rotating stud. The first limit nut 6222 is threadedly engaged with the first rotating stud to limit the axial displacement of the first drive wheel 6221. The second drive wheel assembly 623 includes a second drive wheel 6231 and a second limit nut 6232. The second drive wheel 6231 is rotatably sleeved on the second rotating stud, and the second limit nut 6232 is threadedly engaged with the second rotating stud to limit the axial displacement of the second drive wheel 6231.

Figure 7:
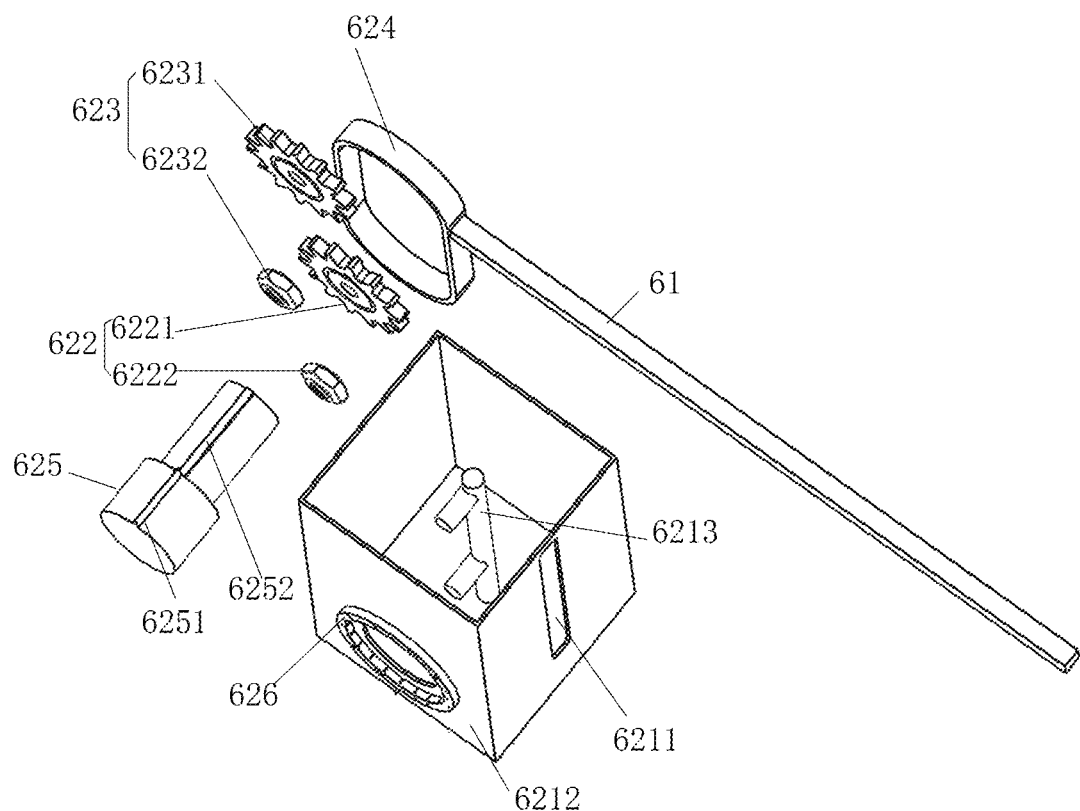
FIG. 7 is an exploded structural diagram of the injection volume control mechanism in FIG. 4.

Specifically, as shown in FIG. 7, in one embodiment, a key slot is provided on the first drive wheel 6221, and a drive key 6252 is provided on the knob 625, which is engaged with the key slot. When the knob 625 rotates, the drive key 6252 is capable of driving the first drive wheel 6221 to rotate.

Of course, in alternative embodiments that are not shown in the figures, one end of the piston linkage rod 61 is connected to the transmission member 624, and the knob 625 partially extends into the housing 621 and is connected to the second drive wheel assembly 623. Rotating the knob 625 can drive the second drive wheel assembly 623 to rotate, causing the transmission member 624 to transmit between the first drive wheel assembly 622 and the second drive wheel assembly 623, thereby driving the piston linkage rod 61 to slide along the first direction within the limiting sliding groove.

Specifically, as shown in FIGS. 4 to 7, in one embodiment, both the first drive wheel 6221 and the second drive wheel 6231 are sprocket wheels, and the transmission member 624 is a transmission chain.

It should be noted that, depending on the actual situation, it can be decided whether to add a tensioning device to tighten the transmission chain.

Specifically, in one embodiment, the dynamic value of the liquid level difference $\Delta H$ includes $\Delta H_i$ and $\Delta H_e$, where $\Delta H_i$ is height of an initial liquid level difference $\Delta H$, and $\Delta H_e$ is height of a liquid level difference $\Delta H$ after the capillary pressure and the weight of the liquid column corresponding to the liquid level difference $\Delta H$ are balanced. The formula for calculating the imbibition dynamic and resistance ratio $\eta$ of the tested liquid is: $\eta = \Delta H_i / \Delta H_e \times 100\%$.

It should be noted that after adding a certain amount of surfactant solution to the water tank, a certain amount of tiny crude oil droplet is injected into the top of the liquid level in the capillary tube using a syringe. Due to the capillary force, the surfactant solution inside the capillary will be higher than the liquid level in the water tank; the liquid column height (the liquid level difference $\Delta H$ between the liquid level in the capillary 20 and the liquid level in the tank 10) satisfies:

$$p_c = \frac{2\sigma \cos\theta}{r} = \rho g \Delta H;$$

where $P_c$ is the capillary force, $\sigma$ is the oil-water interfacial tension, $\theta$ is the wetting angle of the surfactant solution (the contact angle between the surfactant solution and the glass capillary wall), r is the radius of the glass capillary, $\rho$ is the average density of the oil-water liquid column above the liquid level in the water tank, and g is Gravitational acceleration, and $\Delta H$ is the liquid level difference between the liquid level in the capillary and the liquid level in the tank.

It can be seen that the liquid level difference $\Delta H$ is inversely proportional to the wetting angle $\theta$ of the surfactant solution and directly proportional to the oil-water interfacial tension $\sigma$. The process of the whole system reaching stability is a process in which both $\theta$ and $\sigma$ decrease. The former makes $\Delta H$ increase with time, and the latter makes $\Delta H$ decrease with time.

Because the time required for the wetting angle to reach a stable value is different from that of interfacial tension. The height of the above liquid column will increase or decrease with time. Because imbibition mainly occurs in the initial stage of contact between the surfactant solution and the crude oil, higher capillary force in this stage can effectively promote imbibition effect. As time goes on, imbibition weakens gradually and enters the stage of displacement, in which higher capillary force will produce serious Jarmin's effect, thus inhibiting displacement effect. It can be seen that the initial capillary force mainly acts as the driving force for the oil displacement by imbibition, while the later capillary force acts mainly as the resistance for the oil displacement by imbibition. Under the condition of different concentration of the surfactant solution, the changes in the liquid column height ΔH over time can reflect the changes in capillary force, and then the optimal concentration of the surfactant solution can be determined through the ratio of $\Delta H_i$ to $\Delta H_e$.

On this basis, the above imbibition dynamic and resistance ratio is defined as:

$$\eta = P_{ci}/P_{ce} \times 100\% = \Delta H_i/\Delta H_e \times 100\%;$$

where η is the imbibition dynamic and resistance ratio, describing the balance between the initial imbibition capillary driving force and the later oil displacement capillary resistance. A larger value is more favorable for surfactant oil displacement. $P_{ci}$ is the initial capillary force; $P_{ce}$ is the capillary force after equilibrium; $\Delta H_i$ is the height of the initial liquid level difference ΔH; and $\Delta H_e$ is the height of the liquid level difference ΔH after equilibrium. The imbibition dynamic and resistance ratio for each concentration is calculated. The concentration corresponding to the maximum imbibition dynamic and resistance ratio is preferred, and the optimal concentration of the surfactant solution is selected, considering the cost of use.

Second Embodiment

Figure 11:
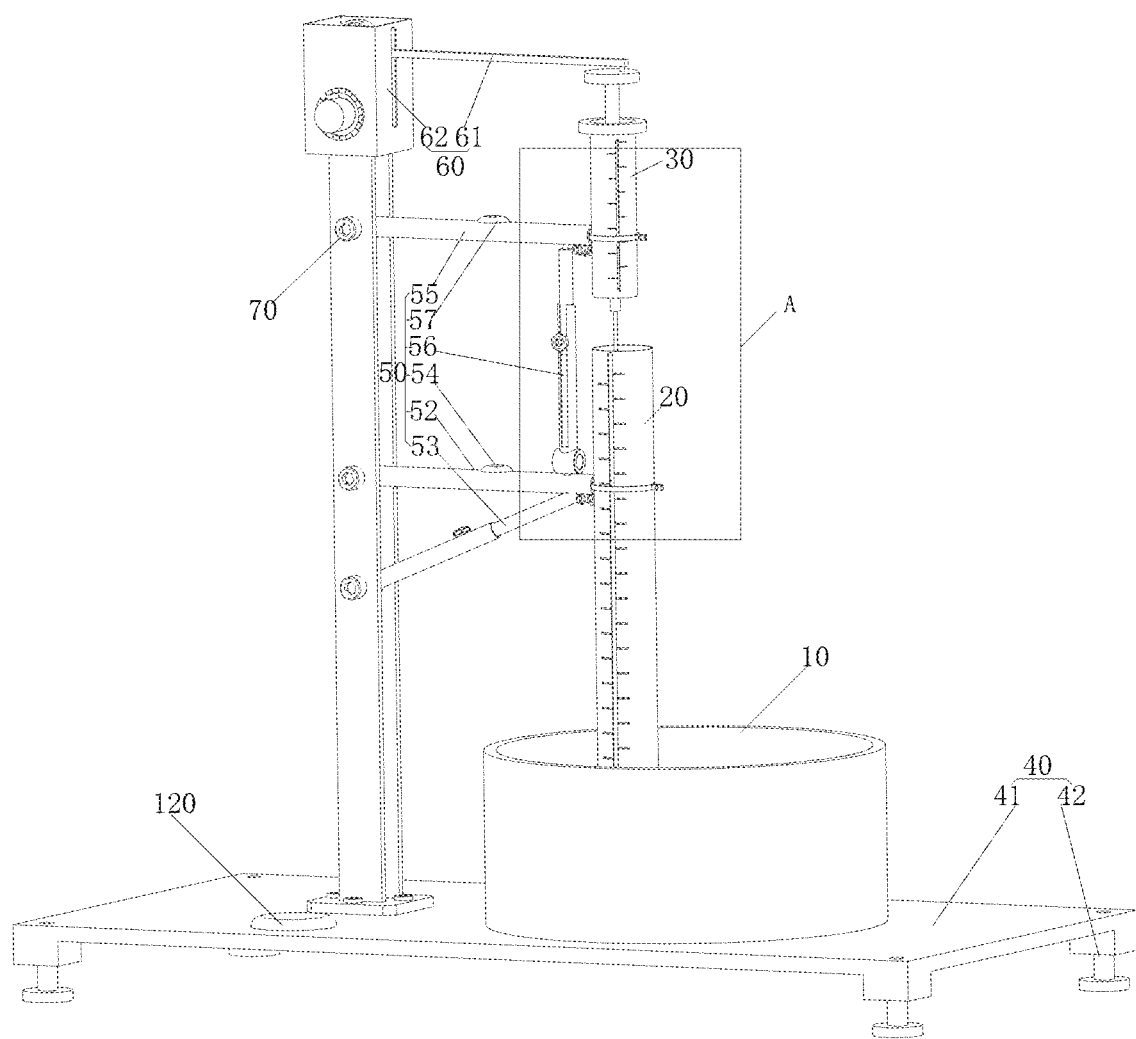
FIG. 11 is a schematic structural diagram of a device for determining the surfactant concentration for oil displacement by imbibition according to the second embodiment.
Figure 12:
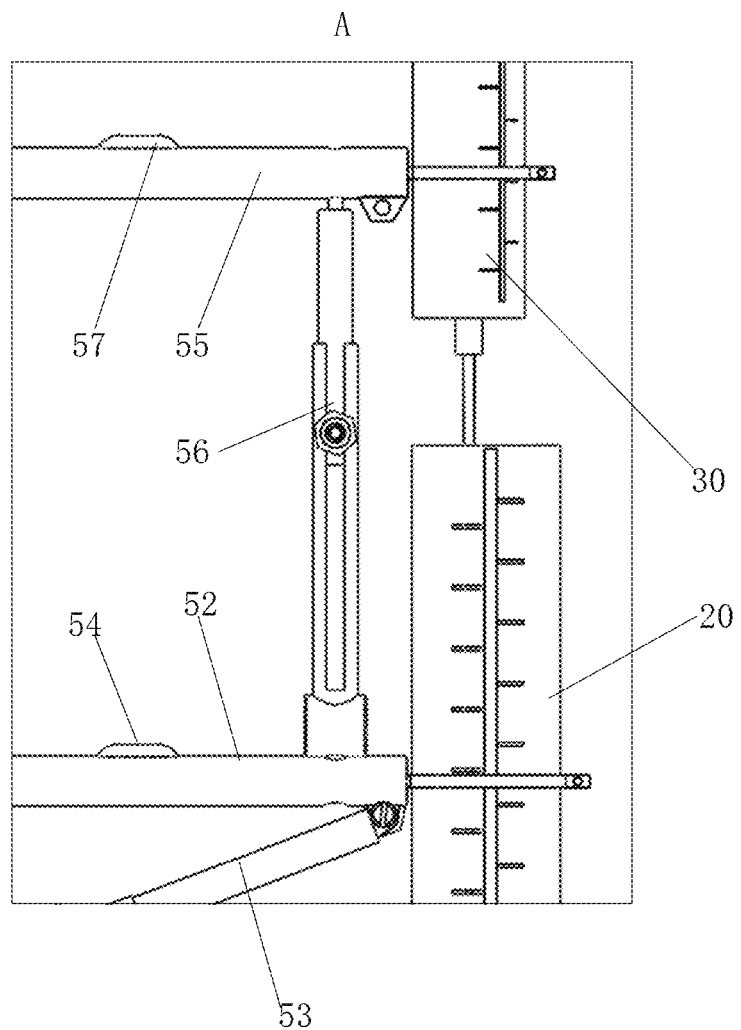
FIG. 12 is a partial enlarged view at point A in FIG. 11.

The Second Embodiment differs from the First Embodiment in the following aspects:

Specifically, as shown in FIGS. 11 and 12, one end of the second telescopic rod 56 is connected to the syringe holder 55. The other end of the second telescopic rod 56 is connected to the capillary tube holder 52.

Figure 13:
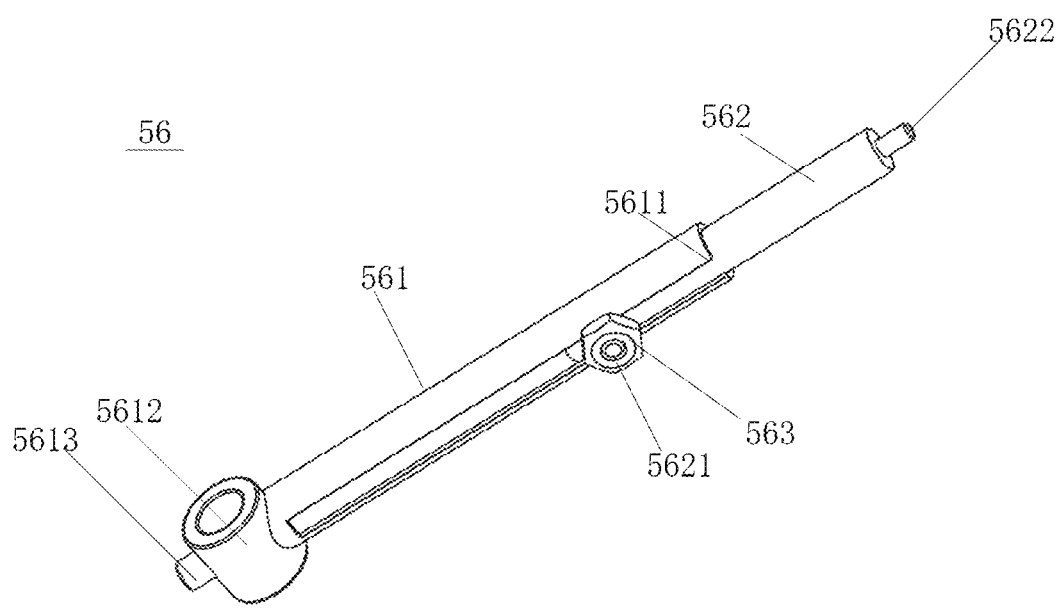
FIG. 13 is a schematic structural diagram of a second telescopic rod in FIG. 11.

Specifically, as shown in FIGS. 12 and 13, the second telescopic rod 56 includes a second outer cylinder 561 and a second inner cylinder 562 arranged telescopically within the second outer cylinder 561. The second outer cylinder 561 is inserted and connected with the capillary tube holder 52, and the second inner cylinder 562 is threadedly connected with the syringe holder 55.

Specifically, as shown in FIG. 13, one end of the second inner cylinder 562 is provided with a second connecting sleeve 5612. The second connecting sleeve 5612 is provided with an inserting post 5613. The capillary tube holder 52 is provided with an inserting hole, and the inserting post 5613 is inserted into the inserting hole. One end of the second inner cylinder 562 is provided with a connecting post 5622, and a connecting hole is disposed in the syringe holder 55. The connecting post 5622 is inserted into the connecting hole. In this embodiment, the connecting hole is a threaded hole, and the connecting post 5622 is a threaded post.

Specifically, as shown in FIG. 13, a second stud 5621 is arranged on the outer periphery of the second inner cylinder 562, and a second opening sliding groove 5611 is arranged on the outer periphery of the second outer cylinder 561 along the axial direction. The second stud 5621 is slidably engaged with the second opening sliding groove 5611, allowing the second outer cylinder 561 is telescopically engaged with the second inner cylinder 562. One end of the second stud 5621 extends out of the second opening sliding groove 5611. The second telescopic rod 56 further includes a second nut 563. The second nut 563 is threadedly engaged with one end of the second stud 5621 extending out of the second opening sliding groove 5611. When the second inner cylinder 562 is moved to the position where the syringe holder 55 is leveled, the second nut 563 is tightened to fix the relative position between the second inner cylinder 562 and the second outer cylinder 561.

It should be noted that in the first embodiment, the leveling methods of the syringe holder 55 and capillary tube holder 52 are independently adjusted with no correlation. In the second embodiment, the leveling methods of the syringe holder 55 and capillary tube holder 52 are interrelated. First, the leveling of the capillary tube holder 52 must be completed, and only after that can the leveling of the syringe holder 55 be completed.

It can be adjusted according to the actual situation that in both first and second embodiment, the first drive wheel and second drive wheel can be pulleys, and the transmission member 624 can be a belt, with the belt connected to one end of the piston linkage rod 61.

It can also be adjusted according to the actual situation that both the first and second telescopic rods can be hydraulic cylinders, with a driving end connected to the syringe holder 55 or the capillary tube holder 52. Leveling of the syringe holder 55 or the capillary tube holder 52 is achieved by telescoping of the driving end.

It can also be adjusted according to the actual situation that the first telescopic rod can be a hydraulic cylinder, and the second telescopic rod can adopt the structures from the above first and second embodiments.

It can also be adjusted according to the actual situation that both the first and second telescopic rods can use electric push rods for driving.

Figure 14:
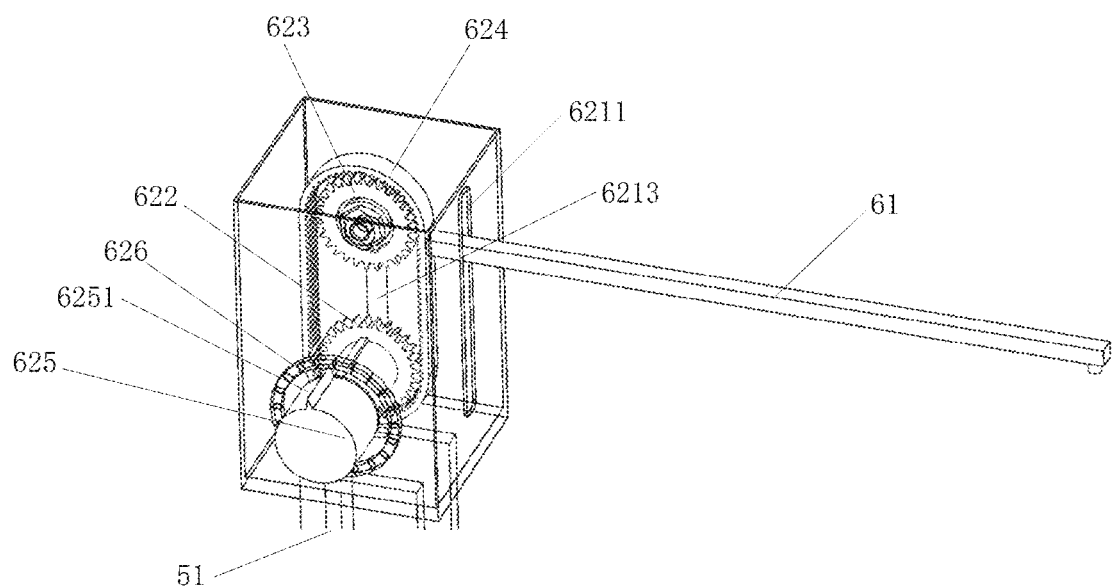
FIG. 14 is a perspective view of an injection volume control mechanism in FIG. 11.

Specifically, as shown in FIG. 14, both the first drive wheel 6221 and the second drive wheel 6231 are gears, and the transmission member 624 is an annular rack, with both the first drive wheels 6221 and the second drive wheel 6231 engaged with the transmission member 624.

Other structures in the Second Embodiment are the same as those for the First Embodiment, and are not described here.

Third Embodiment

The disclosure further provides a method for determining concentration of a surfactant solution for oil displacement by imbibition, which employs the device from the first embodiment.

Specifically, in one embodiment, the method includes:
Step 1: add the tested liquid with a first preset concentration into the tank until the liquid level of the surfactant solution is above the minimum scale of the capillary tube;
Step 2: inject a certain amount of crude oil into the capillary tube;
wherein after injecting crude oil into the capillary tube, a liquid level difference ΔH is generated between a liquid level of the capillary tube and a liquid level of the tank, the liquid level difference ΔH is a dynamic value which varies over time;
Step 3: record the data of the liquid level difference ΔH varying over time;
Step 4: calculate an imbibition dynamic and resistance ratio of the surfactant solution with the first preset concentration based on the data;
Step 5: judge the oil displacement effect of the surfactant solution based on the imbibition dynamic and resistance ratio.

According to the above steps, the imbibition dynamic and resistance ratio corresponding to the surfactant solution is calculated through the liquid level difference ΔH in the disclosure. By comparing the imbibition dynamic and resistance ratios, the oil displacement effect of the surfactant solution can be determined; that is, a larger imbibition dynamic and resistance ratio indicates a better oil displacement effect of the corresponding surfactant solution. This enables the device to quickly determine the impact of surfactant concentration on oil displacement effect, thereby shortening the time required for the determination and selection of the optimal surfactant concentration, improving the efficiency of surfactant selection, and saving costs.

Specifically, in one embodiment, the method includes the following steps:
Step 1: add the surfactant solution with a first preset concentration into the tank until the liquid level of the surfactant solution is above the minimum scale of the capillary tube; Step 2: inject 0.01 mL of crude oil into the capillary tube;
Step 3: record the data of the liquid level difference ΔH varying over time;
Step 4: calculate an imbibition dynamic and resistance ratio of the surfactant solution with the first preset concentration based on the data;
Step 5: clean the water tank and the capillary tube;
Step 6: add the surfactant solution with a second preset concentration into the tank until the liquid level of the surfactant solution is above the minimum scale of the capillary tube;
Step 7: repeat steps 2 to 4 to calculate an imbibition dynamic and resistance ratio of the surfactant solution with the second preset concentration;
Step 8: clean the water tank and the capillary tube;
Step 9: add the surfactant solution with a third preset concentration into the tank until the liquid level of the surfactant solution is above the minimum scale of the capillary tube;
Step 10: repeat steps 2 to 4 to calculate an imbibition dynamic and resistance ratio of the surfactant solution with the third preset concentration;
Step 11: clean the water tank and the capillary tube;
Step 12: add the surfactant solution with a fourth preset concentration into the tank until the liquid level of the surfactant solution is above the minimum scale of the capillary tube;
Step 13: repeat steps 2 to 4 to calculate an imbibition dynamic and resistance ratio of the surfactant solution with the fourth preset concentration;
Step 14: determine the oil displacement effect of the surfactant solution with the first to fourth preset concentrations according to the corresponding imbibition dynamic resistance ratios;

Among them, the larger the imbibition dynamic and resistance ratio, the better the displacement effect of the surfactant solution with corresponding concentration.

Figure 15:
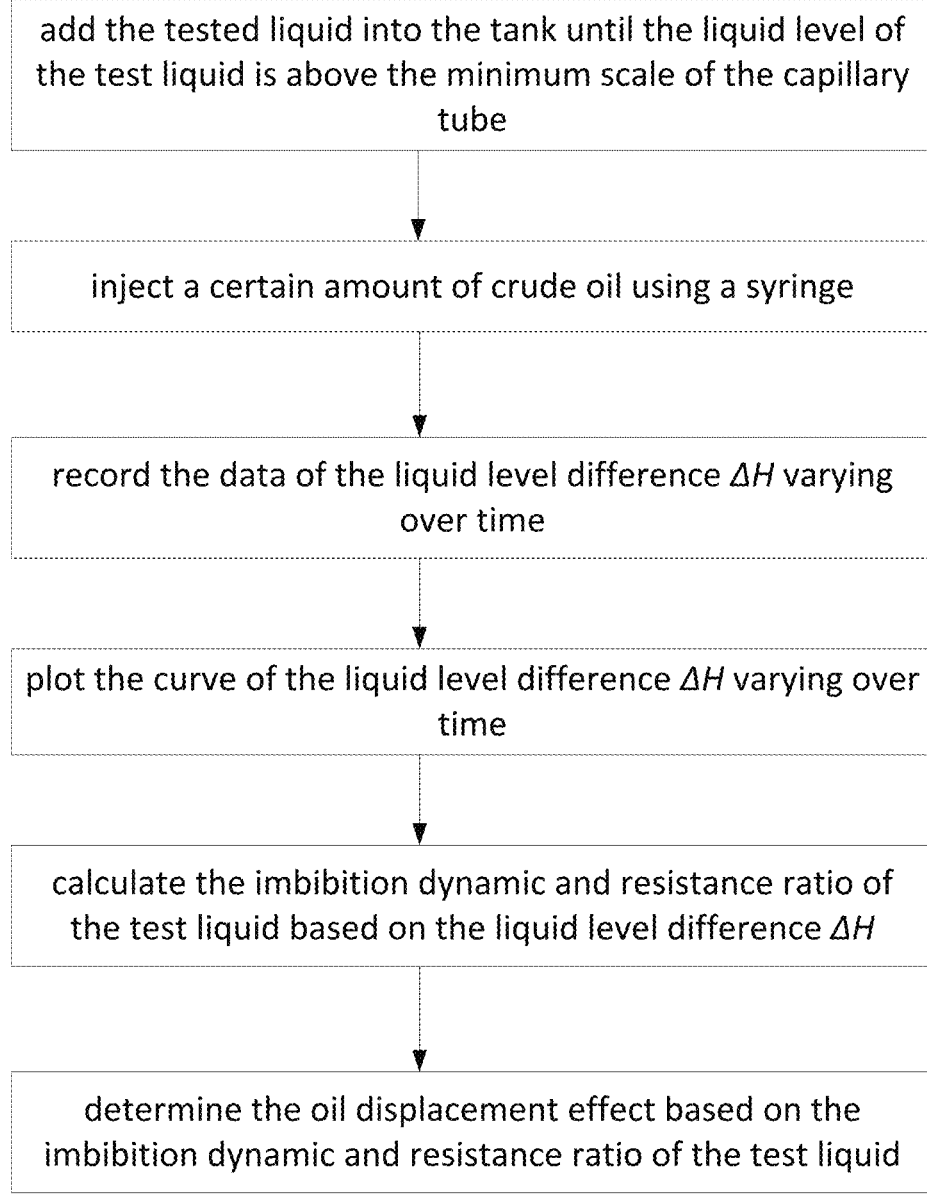
FIG. 15 is a flowchart of a method for determining the surfactant concentration for oil displacement by imbibition according to the third embodiment.

Specifically, as shown in FIG. 15, in one embodiment, the method includes the following steps:
add the tested liquid into the tank until the liquid level of the tested liquid is above the minimum scale of the capillary tube;
inject a certain amount of crude oil using a syringe;
record the data of the liquid level difference ΔH varying over time;
plot the curve of the liquid level difference ΔH varying over time;
calculate the imbibition dynamic and resistance ratio of the tested liquid based on the liquid level difference ΔH;
determine the oil displacement effect based on the imbibition dynamic and resistance ratio of the tested liquid.

The tested liquid can be water used as blank control or surfactant solutions of different concentrations.

Based on the third embodiment, the disclosure provides four more complete and specific application embodiments:

First Application Embodiment

Figure 16:
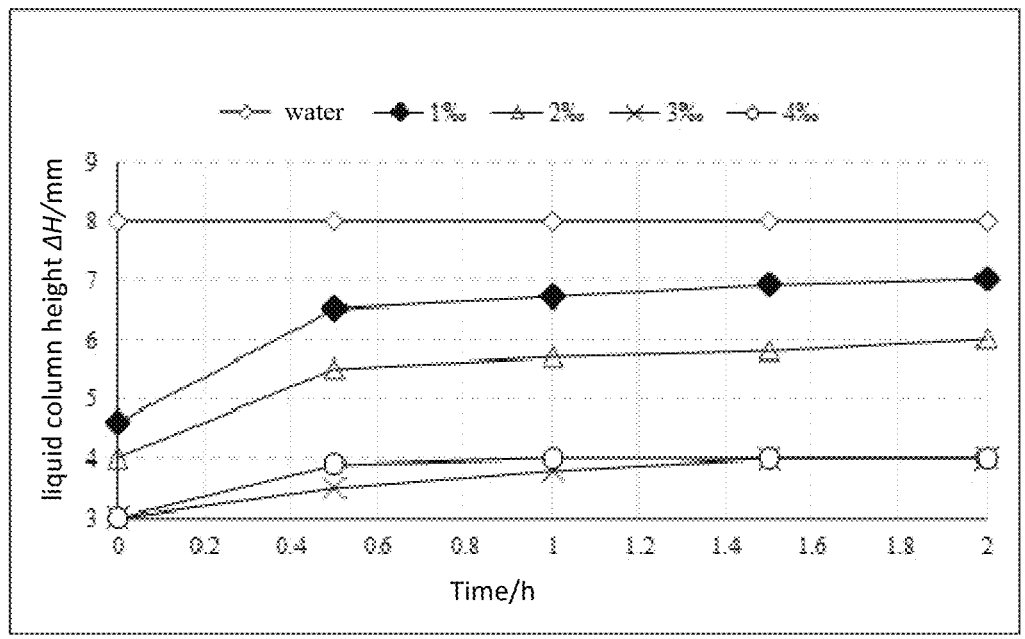
FIG. 16 is a test result curve of different concentrations of anionic surfactant SLES solution according to the first application embodiment.

As shown in FIG. 16, the disclosure also provides a method to determine the surfactant concentration for oil displacement by imbibition, which employs the device from the first embodiment. The method includes the following steps:
Step 1: prepare 20 mL of crude oil, and 500 mL of tap water and 500 mL of sodium lauryl ether sulfate (SLES) solutions with mass concentration of 1‰, 2‰, 3‰ and 4‰ for testing;
Step 2: assemble the testing device. Adjust the four anchor bolts at the bottom of the base to level the third spirit level, and place the water tank on top of the base. The metal bracket is connected to the base with through screws at the bottom. The left end of the capillary tube holder and the left end of the syringe holder are rotatably connecting with the metal bracket. Adjust the height of the right end of the capillary tube holder to keep the spirit level horizontal. Fix the capillary on the capillary tube holder through fastening screws, and the lower end of the capillary is more than 2 mm away from the bottom of the water tank. Adjust the height of the right end of the syringe holder to keep the spirit level horizontal, and fix the syringe containing crude oil on the syringe holder through fastening screws. The left side of the injection quantity control mechanism is fixed on the upper end of the metal bracket, and the right side of the injection quantity control mechanism is fixedly connected with the piston of the syringe through a precise buckle;
Step 3: add water to the water tank until the liquid level is 1 cm above the minimum scale line of the capillary tube;
Step 4: rotate the knob to inject 0.01 mL of crude oil into the capillary tube;
Step 5: record the height ΔH of the liquid column at the top of the oil drop in the capillary above the liquid level in the tank and its variation with time;
Step 6: clean the capillary tube and water tank, then sequentially replace the water with SLES solutions with concentrations of 1‰, 2‰, 3‰, and 4‰, repeating steps 3, 4, and 5.
Step 7: plot the curves of ΔH varying over time under different surfactant concentration conditions (FIG. 16).

The results shown in FIG. 16 indicate that, firstly, due to the reduction in surface tension σ, the liquid column heights of the SLES solutions are all lower than those measured with water; secondly, the measured liquid column heights of the SLES solutions increase over time. Based on the principles of capillary force:

$$p_c = \frac{2\sigma \cos\theta}{r} - \rho g \Delta H$$

It can be seen that the liquid column height ΔH is positively linearly related to the capillary force $P_c$, indicating that within the tested concentration range, the overall process of capillary force equilibrium is characterized by the increase in capillary force resulting from the decrease in wetting angle θ. The imbibition dynamic and resistance ratio is defined by the formula:

$$\eta = P_{ci}/P_{ce} \times 100\% = \Delta H_i/\Delta H_e \times 100\%;$$

where η is the imbibition dynamic and resistance ratio, describing the balance between the initial imbibition capillary driving force and the later oil displacement capillary resistance. A larger value is more favorable for surfactant oil displacement. $P_{ci}$ is the initial capillary force; $P_{ce}$ is the capillary force after equilibrium; $\Delta H_i$ is the height of the initial liquid level difference ΔH; and $\Delta H_e$ is the height of the liquid level difference ΔH after equilibrium. The imbibition dynamic and resistance ratios for the concentrations of 1‰, 2‰, 3‰, and 4‰ were calculated to be 66%, 68%, 75%, and 75%, respectively (see Table 1).

TABLE 1

Surfactant SLES Test Data Table

| Con-centration | Liquid Column Height (mm) | | | | | Imbibition dynamic and resistance ratio $\Delta H_i/\Delta H_e$ (%) |
| --- | --- | --- | --- | --- | --- | --- |
| | 0 h | 0.5 h | 1.0 h | 1.5 h | 2.0 h | |
| 0 | 8 | 8 | 8 | 8 | 8 | 100 |
| 1‰ | 4.6 | 6.5 | 6.7 | 6.9 | 7 | 66 |
| 2‰ | 4 | 5.5 | 5.7 | 5.8 | 6 | 67 |
| 3‰ | 3 | 3.5 | 3.8 | 4 | 4 | 75 |
| 4‰ | 3 | 3.9 | 4 | 4 | 4 | 75 |

Therefore, the optimal concentrations corresponding to the maximum imbibition dynamic and resistance ratio are approximately 3‰ to 4‰. Considering usage costs, the best usage concentration of SLES is preferred to be around 3‰.

Second Application Embodiment

The second application embodiment is substantially that same as the first application embodiment except that the SLES solution is replace with the commercial surfactant SP-1 solution.

Figure 17:
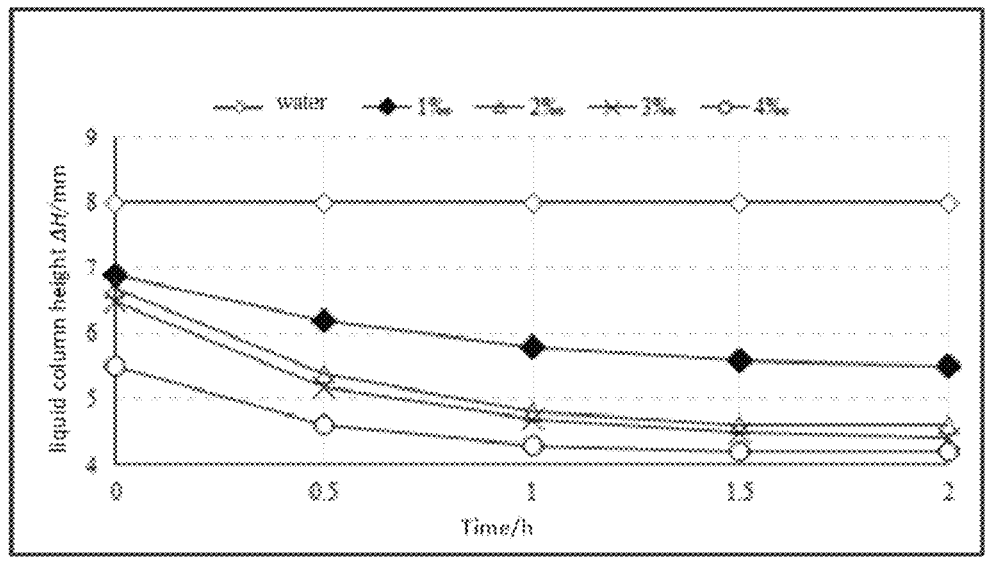
FIG. 17 is a test result curve of different concentrations of commercial surfactant SP-1 solution according to the second application embodiment.

The results shown in FIG. 17 indicate that, firstly, due to the reduction in surface tension σ, the liquid column heights of the SP-1 solutions are all lower than those measured with water; secondly, the measured liquid column heights of the SP-1 solutions decrease over time. Based on the principles of capillary force that within the tested concentration range, the overall process of capillary force equilibrium is characterized by the increase in capillary force. The imbibition dynamic and resistance ratios for the concentrations of 1‰, 2‰, 3‰, and 4‰ % were calculated to be 125%, 146%, 148%, and 131%, respectively (see Table 2).

TABLE 2

Surfactant SP-1 Test Data Table

| Con-centration | Liquid Column Height (mm) | | | | | Imbibition dynamic and resistance ratio $\Delta H_i/\Delta H_e$ (%) |
| --- | --- | --- | --- | --- | --- | --- |
| | 0 h | 0.5 h | 1.0 h | 1.5 h | 2.0 h | |
| 0 | 8 | 8 | 8 | 8 | 8 | 100 |
| 1‰ | 6.9 | 6.2 | 5.8 | 5.6 | 5.5 | 125 |
| 2‰ | 6.7 | 5.4 | 4.8 | 4.6 | 4.6 | 146 |
| 3‰ | 6.5 | 5.2 | 4.7 | 4.5 | 4.4 | 148 |
| 4‰ | 5.5 | 4.6 | 4.3 | 4.2 | 4.2 | 131 |

Therefore, after comprehensively considering the concentration and imbibition and dynamic resistance ratio, the optimum imbibition and displacement concentration of SP-1 is about 2‰.

Third Application Embodiment

The third application embodiment is substantially that same as the first application embodiment except that the SLES solution is replace with the commercial surfactant FH-1 solution.

Figure 18:
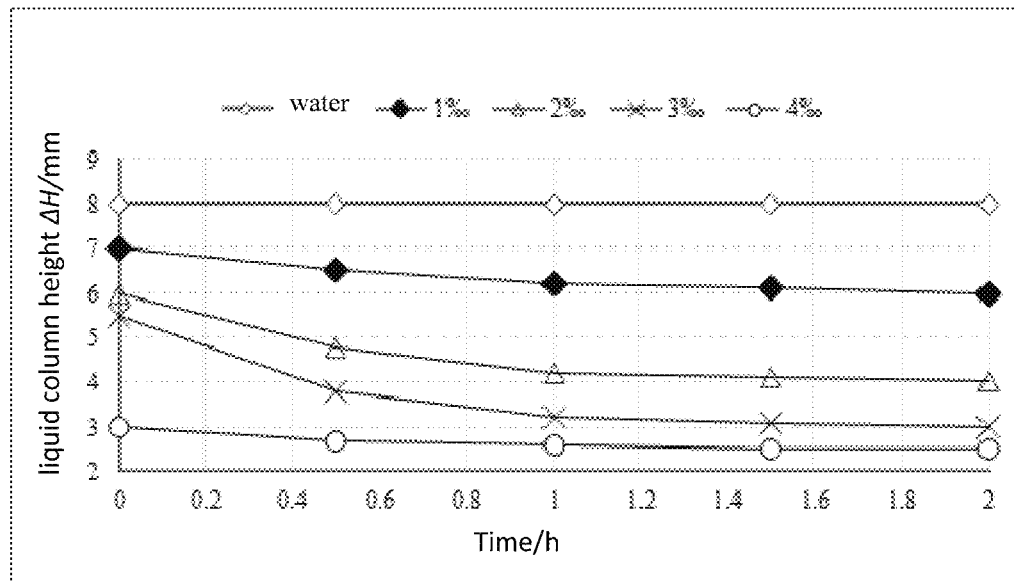
FIG. 18 is a test result curve of different concentrations of composite surfactant FH-1 solution according to the third application embodiment.

The results shown in FIG. 18 indicate that, firstly, due to the reduction in surface tension σ, the liquid column heights of the FH-1 solutions are all lower than those measured with water; secondly, the measured liquid column heights of the FH-1 solutions decrease over time. Based on the principles of capillary force that within the tested concentration range, the overall process of capillary force equilibrium is characterized by the increase in capillary force. The imbibition dynamic and resistance ratios for the concentrations of 1‰, 2‰, 3‰, and 4‰ were calculated to be 117%, 150%, 183%, and 120%, respectively (see Table 3).

TABLE 3

Surfactant FH-1 Test Data Table

| Con-centration | Liquid Column Height (mm) | | | | | Imbibition dynamic and resistance ratio $\Delta H_i/\Delta H_e$ (%) |
| --- | --- | --- | --- | --- | --- | --- |
| | 0 h | 0.5 h | 1.0 h | 1.5 h | 2.0 h | |
| 0 | 8 | 8 | 8 | 8 | 8 | 100 |
| 1‰ | 7 | 6.5 | 6.2 | 6.1 | 6 | 117 |
| 2‰ | 6 | 4.8 | 4.2 | 4.1 | 4 | 150 |
| 3‰ | 5.5 | 3.8 | 3.2 | 3.1 | 3 | 183 |
| 4‰ | 3 | 2.7 | 2.6 | 2.5 | 2.5 | 120 |

Therefore, the optimum concentration of FH-1 is about 3‰ corresponding to the maximum imbibition and dynamic resistance ratio.

Fourth Application Embodiment

The imbibition and displacement effects of the preferred surfactants in the above three application embodiments are compared. Firstly, natural tight rock cores saturated with crude oil are fractured to simulate the tight oil reservoir after fracturing. Secondly, water is injected into the fractured core until the water content at the outlet reached 98%, and the water injection extraction degree is calculated. Finally, surfactant solution imbibition and displacement is carried out on the core after water drive, with each surfactant solution injected at a volume of 4 PV. In order to ensure the imbibition time, two injections are carried out. The inlet and outlet valves are closed after the first injection of 2 PV to simulate soaking for 2 h, and then 2 PV is injected again. After the displacement, the produced liquid volume at the outlet is recorded and the recovery degree of surfactant solution imbibition and displacement is calculated.

Figure 19:
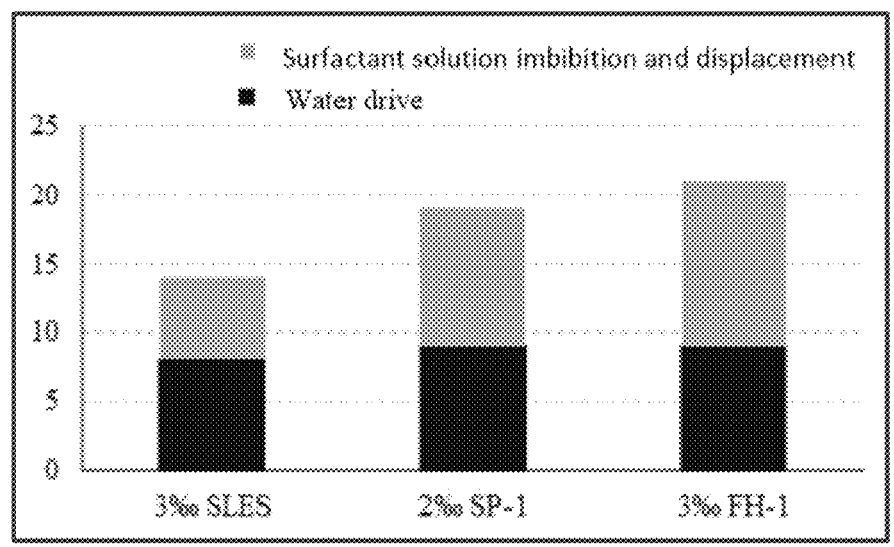
FIG. 19 is a comparison chart for the effects among the SLES solution, the SP-1 solution and the FH-1 solution with optimal concentrations for oil displacement by imbibition according to the fourth application embodiment.

As shown in FIG. 19 and Table 4, the recovery degree at the end of water drive is 8% and 9%. The 3‰ SLES, 2‰ SP-1, and 3‰ FH-1. Imbibition and displacement with 3‰ SLES, 2‰ SP-1 and 3‰ FH-1 can improve the recovery degrees by 6%, 10%, and 12%, respectively, all achieving good effects. Among them, 3‰ FH-1 exhibited the best improvement in recovery rate, which is consistent with its highest capillary dynamic resistance ratio.

As shown in FIG. 19 and the results in Table 4 below, the recovery degree at the end of water drive is 8%-9%, and 3‰ SLES, 2‰ SP-1 and 3‰ FH-1 imbibition and displacement improve the recovery degree by 6%, 10% and 12%. All three have achieved good imbibition and displacement effect, among which 3‰ FH-1 has the best effect in recovery rate, which is consistent with the highest imbibition and dynamic resistance ratio.

TABLE 4

Data of Three Optimal Surfactant Concentration for Oil Displacement by Imbibition

| | Recovery Degree (%) | |
|---|---|---|
| Surfactant | Water drive | surfactant solution imbibition and displacement |
| 3‰ SLES | 8 | 6 |
| 2‰ SP-1 | 9 | 10 |
| 3‰ FH-1 | 9 | 12 |

Although the disclosure has been described with reference to preferred embodiments, various modifications may be made thereto and equivalents may be substituted for parts thereof without departing from the scope of the invention. In particular, the technical features mentioned in the various embodiments can be combined in any way as long as there are no structural conflicts. the disclosure is not limited to the specific embodiments disclosed herein but encompasses all technical solutions falling within the scope of the claims.

What is claimed is:

1. A method for selecting an optimal concentration of a surfactant solution from among a set of surfactants having a range of concentrations, wherein the surfactant is for oil displacement by imbibition, comprising steps of:

Step 1: providing a tank for holding the surfactant solution and a capillary tube with one end located inside the tank;

Step 2: adding the surfactant solution with a first preset concentration into the tank until a liquid level of the surfactant solution is above minimum scale of the capillary tube;

Step 3: injecting crude oil into the capillary tube, a liquid level difference ΔH is generated between a liquid level of the capillary tube and the liquid level of the tank, the liquid level difference ΔH is a dynamic value which varies over time; recording data of the liquid level difference ΔH varying over time, and calculating an imbibition dynamic and resistance ratio of the surfactant solution with the first preset concentration based on the data; cleaning the tank and capillary tube;

Step 4: repeating the steps 2) and 3) for each surfactant solution with concentration ranging from a second preset concentration to an Nth (N=3, 4, 5 . . . ) preset concentration to calculate a plurality of corresponding imbibition dynamic and resistance ratios;

Step 5: determining the optimal concentration under the best oil displacement effect of the surfactant solution based on the imbibition dynamic and resistance ratios of the surfactant solutions with concentration ranging from the first to Nth preset concentration wherein the optimal concentration corresponds to the largest imbibition dynamic and resistance ratio;

wherein the imbibition dynamic and resistance ratio of the surfactant solution is calculated using the formula:

$\eta = \Delta H_i / \Delta H_e \times 100\%$;

where η is the imbibition dynamic and resistance ratio, $\Delta H_i$ is a height of the initial liquid level difference ΔH, and $\Delta H_e$ is a height of the liquid level difference ΔH after equilibrium.

2. The method according to claim 1, wherein the surfactant solution is selected from the group consisting of sodium lauryl ether sulfate solution, SP-1 solution, and FH-1 solution.

3. The method according to claim 2, wherein when N is 4, the first preset concentration is 1 wt ‰, the second preset concentration is 2 wt ‰, the third preset concentration is 3 wt ‰, and the fourth preset concentration is 4 wt ‰.

* * * * *